United States Patent [19]
Sutton, Jr. et al.

[11] Patent Number: 5,442,286
[45] Date of Patent: Aug. 15, 1995

[54] EDDY CURRENT ARRAY INSPECTION DEVICE

[75] Inventors: George H. Sutton, Jr.; Francis H. Little, both of Cincinnati; Carl Granger, Jr., West Chester; Philip F. Stapf, Cincinnati, all of Ohio

[73] Assignee: General Electric Company, Cincinnati, Ohio

[21] Appl. No.: 125,469

[22] Filed: Sep. 22, 1993

[51] Int. Cl.6 ............................................. G01N 27/82
[52] U.S. Cl. ..................................... 324/242; 324/219
[58] Field of Search ............... 324/219, 220, 221, 242, 324/262

[56] References Cited

U.S. PATENT DOCUMENTS

| | | | |
|---|---|---|---|
| 2,534,632 | 12/1950 | Smith | 324/221 |
| 2,622,125 | 12/1952 | Bender | 175/183 |
| 4,543,528 | 9/1985 | Baraona | 324/262 |
| 4,593,245 | 6/1986 | Viertl et al. | 324/23 |
| 4,668,912 | 5/1987 | Junker | 324/220 |
| 4,719,422 | 1/1988 | De Walle et al. | 324/238 |
| 5,023,549 | 6/1991 | Dau et al. | 324/220 |
| 5,047,719 | 9/1991 | Johnson et al. | 324/242 |
| 5,315,234 | 5/1994 | Sutton, Jr. et al. | 324/242 |

FOREIGN PATENT DOCUMENTS

| | | |
|---|---|---|
| 152687A1 | 8/1985 | European Pat. Off. . |
| 231865A2 | 8/1987 | European Pat. Off. . |
| 423753A1 | 4/1991 | European Pat. Off. . |
| 450950A2 | 10/1991 | European Pat. Off. . |

OTHER PUBLICATIONS

Patent Abstracts of Japan, vol. 16, No. 52 (E-1164) 10, Feb. 1992 & JP-A-32 54 103 (Kawasaki) 13, Nov. 1991, Abstract.

Database WPI, Week 9002, Derwent Publications Ltd., London, GB; AN 90-008592 & DE-A-39 19 976 (Nippon Antenna) 28, Dec. 1989, Abstract.

"Robot Controlled Inspection of Roto-Symmetrical Parts", by S. Oaten and J. Bertelle, The American Society for Nondestructive Testing, Inc., ASNT Spring Conference, Mar. 30-Apr. 3, 1992, pp. 117-119.

Primary Examiner—Kenneth A. Wieder
Assistant Examiner—Kourosh Cyrus Khosravi
Attorney, Agent, or Firm—Andrew C. Hess; David L. Narciso

[57] ABSTRACT

A device for inspecting a component, such as a dovetail slot of a gas turbine engine or the like, includes an eddy current array circuit having an active face for positioning on the surface of the component during the inspection operation and a backing disposed on a face of the eddy current array circuit opposite to the active face. The eddy current array circuit and the backing are disposed over the operating face and expandable sides of an expandable bar. The expandable bar has a slot formed therein with interior side edges which narrow toward the operating face of the bar at a predetermined slope. An expanding wedge with angled sides is positioned to cause the angled sides to respectively matingly engage the interior sides of the slot to cause the exterior sides of the expandable bar to expand outwardly a greater distance as the wedge is pushed deeper into the slot to cause the eddy current array circuit into conformance with the shape of the surface being inspected.

5 Claims, 4 Drawing Sheets

EDDY CURRENT ARRAY INSPECTION DEVICE

BACKGROUND OF THE INVENTION

The present invention is related to the following patent applications:

Co-pending patent application Ser. No. 07/696,455, entitled "Eddy Current Probe Arrays" by Kristina H. Hedengren et al., which discloses and claims a plurality of spatially correlated eddy current probe elements sufficiently disposed within a flexible interconnecting structure to collect a discrete plurality of spatially correlated eddy current measurements for nondestructive near surface flaw detection. This application is assigned to the same assignee as the present application and is incorporated herein in its entirety by reference.

Patent application Ser. No. 07/696,456, issued as U.S. Pat. No. 5,182,513, entitled Method and Apparatus for a Multi-Channel Multi-Frequency Data Acquisition System for Nondestructive Eddy Current Inspection Testing by John D. Young et al., which discloses and claims a method and apparatus for acquiring a plurality of synchronized, spatially correlated, discrete eddy current measurement signals for image processing. This patent application is also assigned to the same assignee as the present application and is incorporated herein by reference in its entirety.

Patent application Ser. No. 07/696,457, issued as U.S. Pat. No. 5,237,271, entitled: Apparatus and Method for Non-Destructive Testing Using Multi-Frequency Eddy Currents by Kristina H. Hedengren, which discloses and claims a method for improving resolution and characterization in detection of near surface flaws using non-destructive eddy current inspection. This patent application is also assigned to the same assignee as the present application and is incorporated herein by reference in its entirety.

Co-pending patent application Ser. No. 07/504,769, entitled "A Flexible High Density Interconnect Structure and Flexibly Interconnected System" by Charles W. Eichelberger, et al., which describes a multi-layer multi-component integrated fabrication technology suitable for making flexible, spatially correlated, eddy current probe arrays for inspecting surfaces which have complex geometric shapes. This co-pending application is also assigned to the same assignee as the present application and is incorporated herein by reference in its entirety.

Patent application Ser. No. 07/862,699, issued as U.S. Pat. No. 5,262,722, entitled An Apparatus for Near Surface, Nondestructive Eddy Current Scanning of a Conductive Part Using a Multi-Layer Eddy Current Probe Array by Kristina H. Hedengren, et al., filed concurrently herewith, which describes an ultra-thin, flexible, film-like, multi-layer eddy current probe array structure which is configured to provide electrical and mechanical interconnection to respective system electronics and mechanical scanning means. This related application is also assigned to the same assignee as the present application and is incorporated herein by reference in its entirety.

Patent application Ser. No. 07/862,950, issued as U.S. Pat. No. 5,315,234, entitled An Eddy Current Device for Inspecting a Component Having a Flexible Support with a Plural Sensor Array, by George H. Sutton, Jr., et al., which discloses and claims a mechanical apparatus for supporting and deploying an eddy current array circuit to substantially conform to a surface of a workpiece being scanned by the apparatus to inspect the workpiece for defects. This related application is also assigned to the same assignee as the present application and is incorporated herein by reference in its entirety.

BACKGROUND OF THE INVENTION

The present invention relates to the inspection of components using eddy current technology and, more particularly, to a device for inspecting a component having a complex geometric shape, such as a dovetail slot, gear tooth or the like of a gas turbine engine component or similar workpiece using a multiplicity of eddy current probe or circuit elements formed in an array to provide inspection of a larger surface area in a shorter time than has heretofore been available with a substantially lower probability of missing a flaw or defect.

Eddy current inspection is a commonly used technique for detecting discontinuities or flaws in the surface of components such as the components of a gas turbine engine. Eddy current techniques are based on the principle of electromagnetic induction in which eddy currents are induced within the component under inspection. The eddy currents are induced in the component by alternating magnetic fields created in a coil of an eddy current probe, referred to as a drive coil, when the probe is moved into proximity with the component under inspection. Changes in the flow of eddy currents are caused by the presence of a discontinuity or a crack in the test specimen. The altered eddy currents produce a secondary magnetic field which is received by the eddy current probe coil or by a separate sense coil in the eddy current probe which converts the altered secondary magnetic field to an electrical signal which may be recorded on a strip chart or similar device for analysis. An eddy current machine operator may then detect and size flaws by monitoring and analyzing the recorded signals. Flaws or defects are detected if the electrical signal exceeds a predetermined voltage threshold.

One problem with inspecting the surface of a workpiece with an eddy current array is to maintain the array in conformance and/or contact with the surface, as the eddy current device or probe is scanned across the surface, and to cause each of the pluralities of drive and sense elements comprising the eddy current array to be maintained at their respective substantially constant distances from the inspection surface during scanning, preferably at a controlled rate of scan. Additionally, workpiece geometries may vary from one component to another because of manufacturing process variability. Variations in the distance between the drive and sense elements and the inspection surface or a gap between the probe and the inspection surface as the probe is scanned across the surface is referred to as liftoff and is undesirable.

SUMMARY OF THE INVENTION

It is, accordingly, a primary object of the present invention to provide a novel apparatus for inspecting a component which is not subject to the foregoing disadvantages.

It is a further object of the present invention to provide a novel device for inspecting a dovetail slot, gear tooth or the like of a gas turbine engine component or other apparatus in a single pass with the eddy current probe elements being maintained at a substantially constant equal distance from the surface under inspection, during the entire scan.

In accordance with the present invention, the eddy current array inspection device includes an eddy current array circuit having respective pluralities of drive and sense elements and having an active face for positioning on a surface portion of the component during an inspection operation. A backing is disposed on a face of eddy current array circuit opposite to the active face for applying a uniform pressure behind the array circuit to maintain the circuit against the surface portion while scanning across the component during the inspection operation. An expandable bar is provided with exterior side edges and an operating face shaped to cause the eddy current array circuit to conform to the shape of the component surface under inspection. The eddy current array circuit and the backing are disposed over the operating face and the exterior side edges of the expandable bar with the array circuit active face being closest to the component surface portion. The expandable bar has a slot formed therein with the slot having interior sides which narrow toward the operating face of the bar at a predetermined slope. An expanding wedge with similarly angled sides is positioned for respectively matingly engaging the interior sides of the slot to cause the exterior side edges of the expandable bar to expand outwardly a greater distance as the wedge is pushed deeper into the slot. An actuator is provided to push the wedge deeper into the slot and to withdraw the wedge after an inspection for removal of the probe from the dovetail slot or other component. Electrical conductors are provided to electrically connect the eddy current array circuit to an eddy current instrument.

These and other objects of the invention, together with features and advantages thereof, will become apparent from the following detailed specification when read with the accompanying drawings in which like reference numerals refer to like elements.

DETAILED DESCRIPTION OF THE PREFERRED EMBODIMENTS

The present invention will be described with respect to inspecting a dovetail slot of a gas turbine engine rotor, disk or the like; those skilled in the art, however, will recognize that the principles of the present invention could be easily adapted or modified to inspect any component having a simple or complex geometric surface.

Figure 1A:
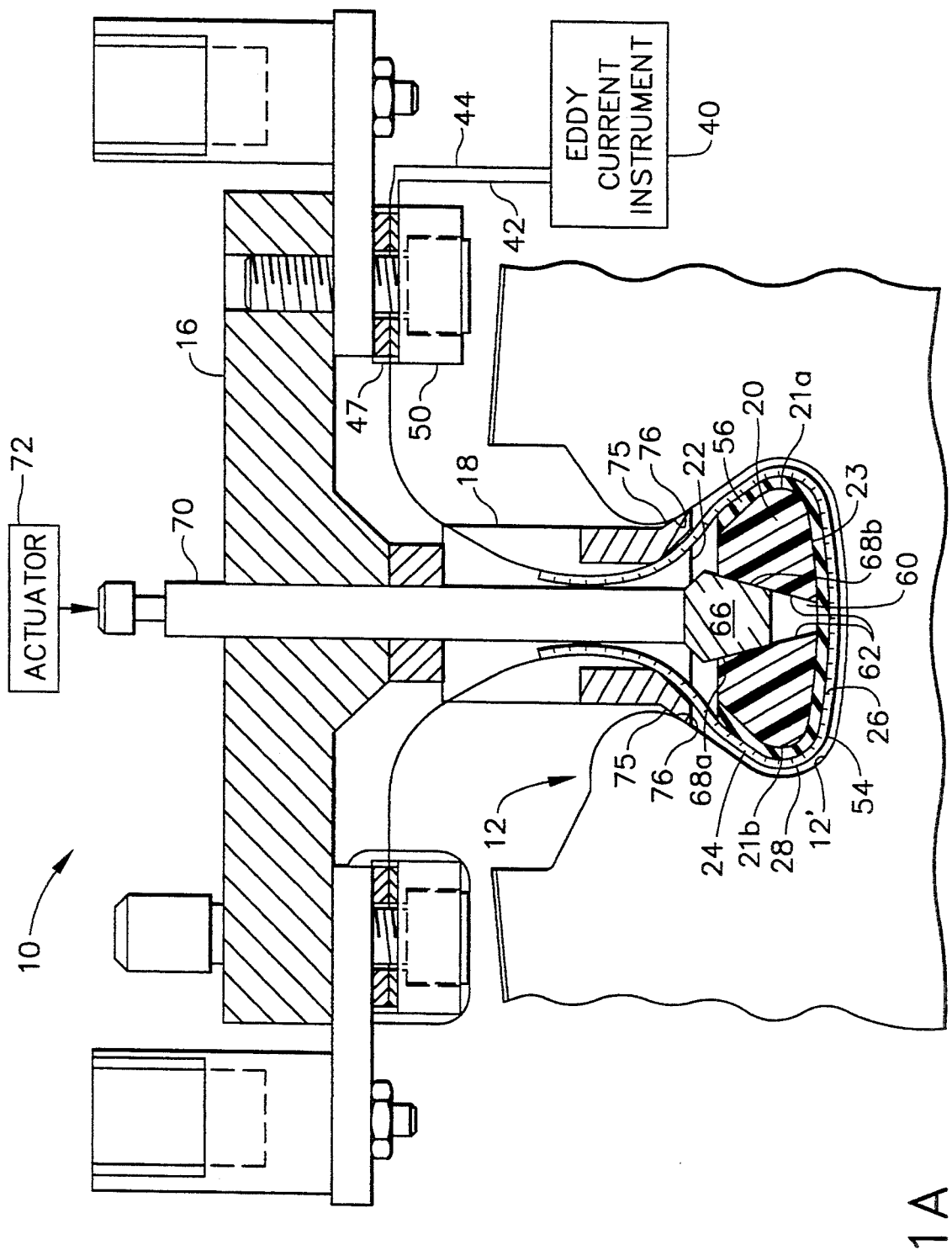
FIG. 1A is a cross-sectional view of an eddy current array probe device in accordance with the present invention in a non-operative position to facilitate insertion into and removal from a dovetail slot of a gas turbine engine component.
Figure 2:
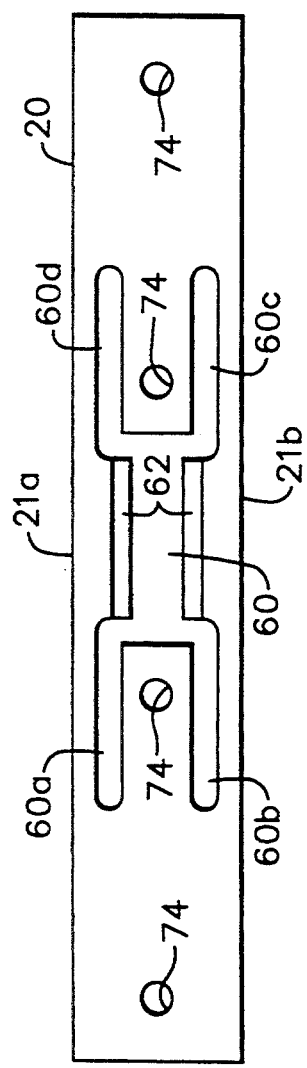
FIG. 2 is a top elevation view of the expandable bar or plate member of the eddy current array probe device of the present invention.

Referring initially to FIG. 1A, the eddy current array probe device 10 for inspecting a complex geometric surface, such as the interior surface of a dovetail slot 12 of a gas turbine engine or the like, includes a probe body base 16 and a probe extension member 18 extending substantially perpendicular to the probe body base 16. An expandable bar or plate 20 is positioned at an end 22 of the probe extension member 18 and is movable between a retracted position proximate to the extension member 18 and an inspection position at a spacing from the extension member 18. Referring also to FIG. 2, the expandable bar 20 has expandable exterior side edges 21a and 21b and an operating face 23 shaped to cause an eddy current array circuit to conform to the shape of the component surface under inspection.

A flexible, compliant backing layer 24 and a flexible, compliant eddy current array circuit 28, disposed over the backing layer 24, are both disposed over the operating face 23 and the expandable side edges 21a and 21b of the expandable bar 20 and extend within the interior of the probe extension member 18 to secure the backing 24 and the eddy current array circuit 28 over the expandable bar 20. The backing layer 24 may be made of a ferrite-containing material to concentrate an electromagnetic flux from the drive coils 30 (FIG. 3) of the eddy current array circuit 28 into the component when each of the drive coils 30 are energized. The compliant backing 24 may have a plurality of ridges 26 formed thereon, which extend substantially parallel to the longitudinal extent of the expandable bar 20 and parallel to the intended direction of scan across the inspection surface, to facilitate disposition of the compliant backing 24 over the expandable bar 20 and to permit the compliant backing 24 to conform to any surface under inspection. The ridges 26 also provide support to prevent the backing 24 from lifting off the surface under inspection as the probe body 16 is moved in the direction parallel to the ridges 26 along the surface for inspection thereof.

Figure 1B:
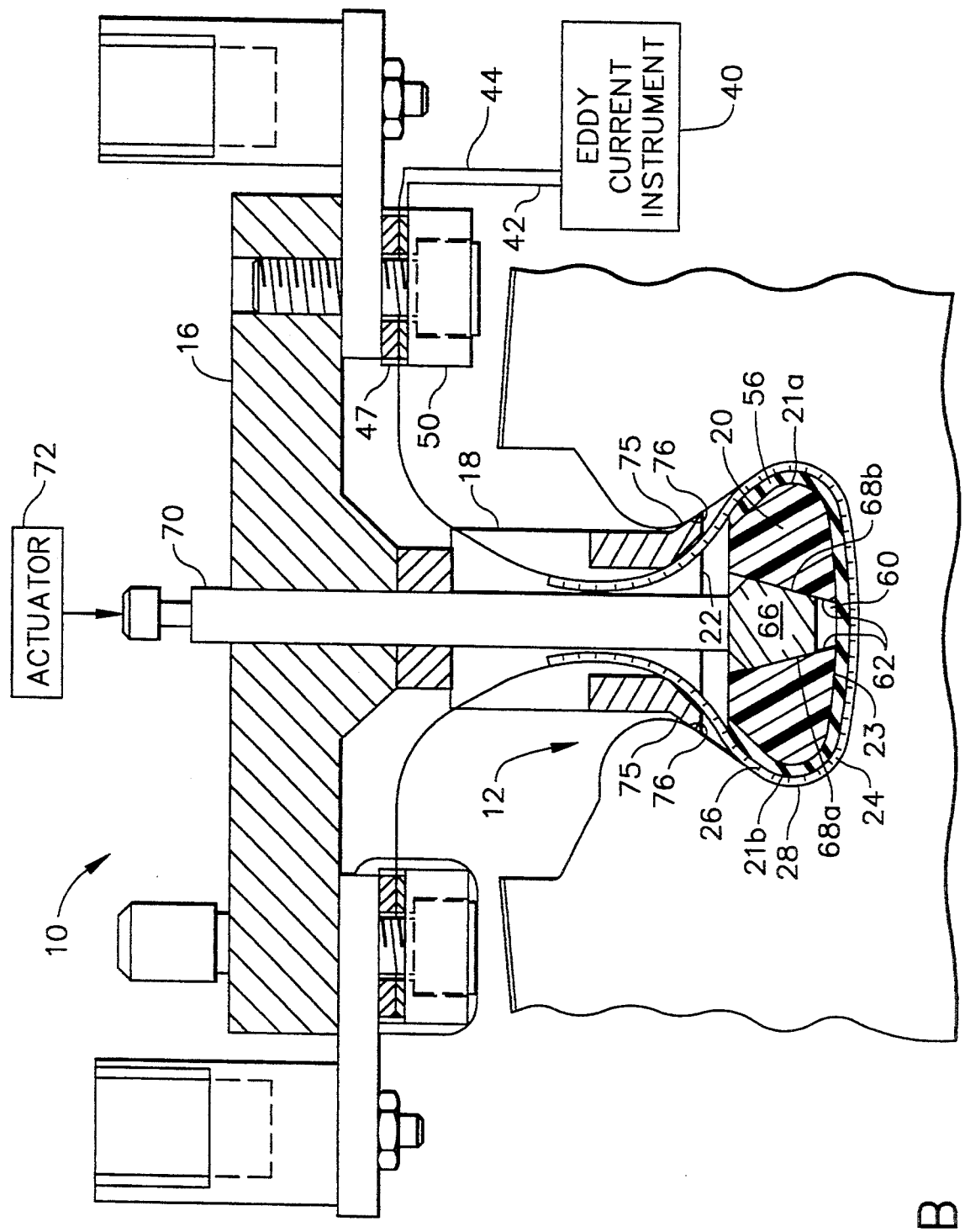
FIG. 1B is a cross-sectional view of the eddy current array inspection device of FIG. 1A in its operative position for scanning along a dovetail slot of a gas turbine engine.
Figure 3:
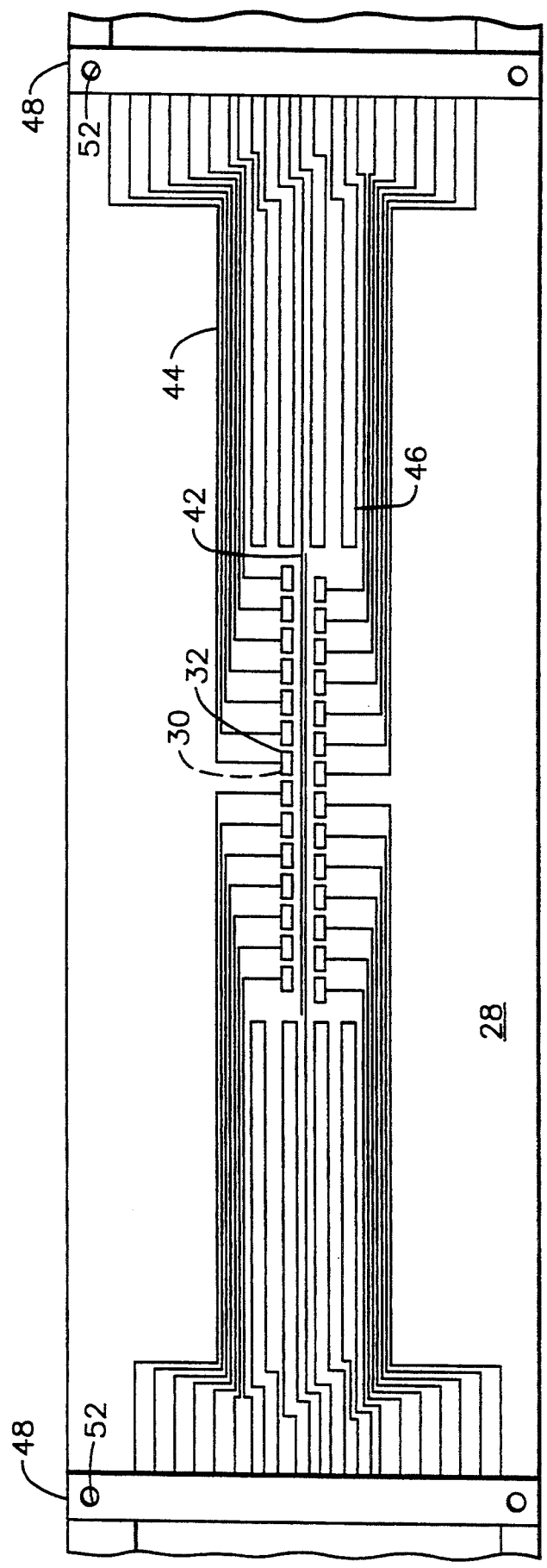
FIG. 3 is a schematic diagram illustrating an example of an eddy current array circuit for use with the present invention.
Figure 4:
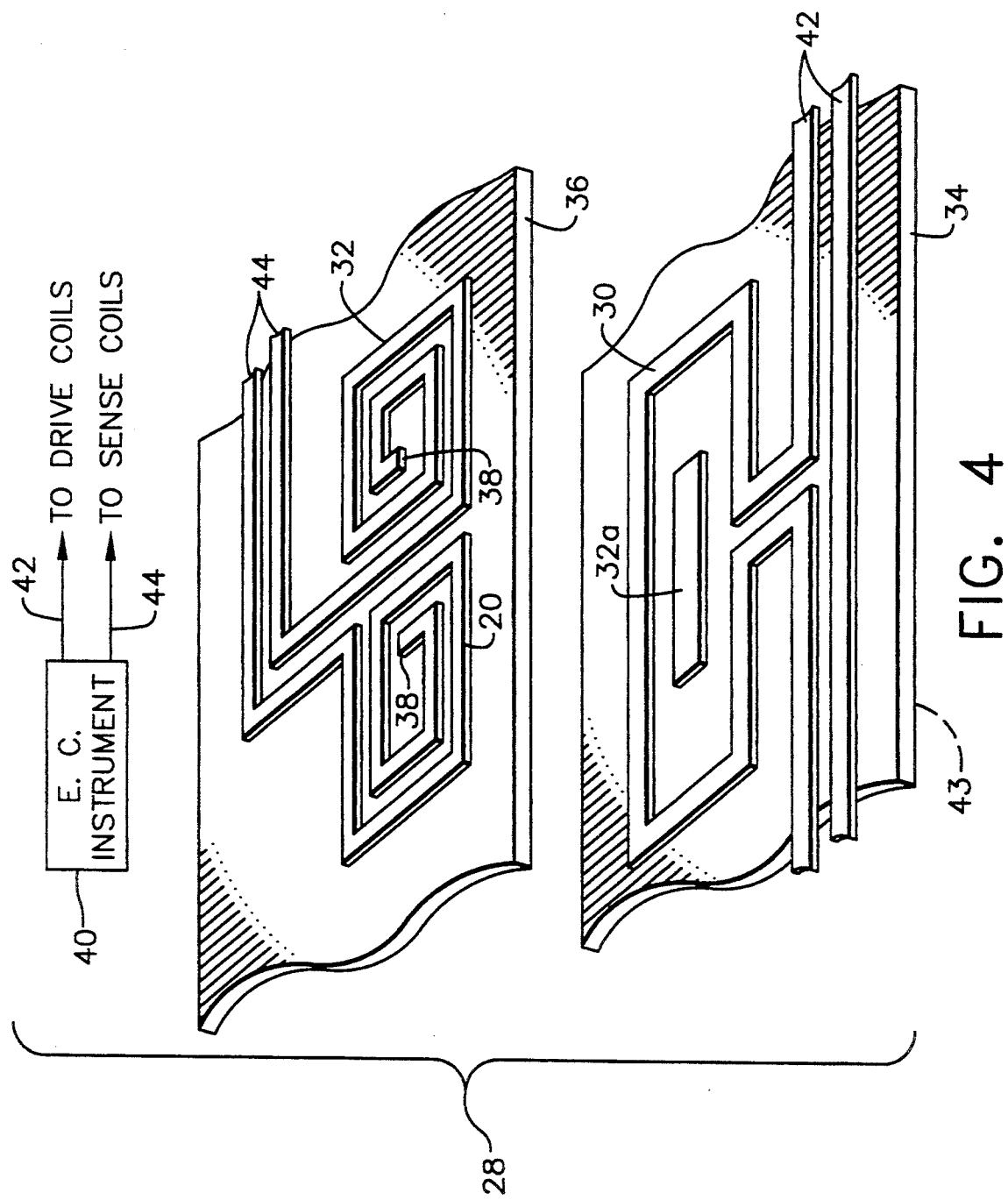
FIG. 4 is a detailed exploded perspective view of a single pair of drive and sense coils or elements of the array of FIG. 3.

The flexible, compliant eddy current array circuit 28 may be similar to those described in co-pending U.S. patent application Ser. No. 07/696,455, entitled "Eddy Current Probe Arrays." An example of an eddy current array circuit 28 which may be used with the eddy current array probe device 10 of the present invention is shown schematically in FIG. 3. The circuit 28 includes a plurality of drive coils 30 and sense coils 32 which may be disposed one above the other in different flexible layers or substrates 34 and 36 as best shown in FIG. 4. The substrates 34 and 36 are shown separated in an exploded perspective view in FIG. 4 for purposes of clarity and explanation. Holes or vias 38 are formed through the substrate 36 for electrically interconnecting the sense coils 32 by a shorting strip 32a disposed on the other substrate 34. Those skilled in the art will recognize that the coils 30 and 32 could also be configured to reside in the same layer or substrate. Electrical contact is made between drive coils 30 and an eddy current instrument 40 (shown schematically in FIG. 4) by conductors 42 and electrical contact is made between the sense coils 32 and the eddy current instrument 40 by conductors 44. As shown in FIG. 3, both conductors 42 and 44 are brought out to the respective outer edges of the substrates 34 and 36 of the eddy current array circuit 28 to provide means for connecting the flexible array circuit 28 to the eddycurrent instrument 40. As shown in FIGS. 1A and 1B, the eddy current circuit 28 is feed up through the interior sides of the probe extension member 18 and the conductors 42 and 44 are connected to the eddy current instrument 40 by a suitable connector represented by reference numeral 47. Conductive shielding strips 46 (FIG. 3) may be disposed between drive lines 42 and sense lines 44 to provide electromagnetic shielding between the conductive lines. Registration plates 48 may be provided to mate with brackets 50 (FIGS. 1A and 1B) to secure the array circuit 28 to the probe body base 16 of the eddy current array probe device 10 and to ensure proper registration of the electrical conductors 42 and 44 for connection to the eddy current instrument 40 and positioning of the drive and sense coils 30 and 32 to provide accurate location and size information of any detected defect during an inspection operation. Registration holes 52 may also be provided or may be provided in place of registration plates 48 to secure array circuit 28 to the probe body base 16 and to provide proper registration of the electrical elements 30 and 32.

Referring back to FIGS. 1A and 1B, the flexible eddy current array circuit 28 has an active face 54 for positioning against the component surface portion, in this case the interior of the dovetail slot 12, during an inspection operation. A protective or sacrificial layer (not shown), such as Kapton TM or Teflon TM, may be disposed over active face 54 to protect the array circuit 28 as it is moved along or scanned along the dovetail slot surface 12' under inspection and to facilitate sliding the active face 54 along the surface.

As previously discussed, the eddy current array circuit 28 is electrically connected to the eddy current instrument 40 by conductors 42 and 44. The eddy current instrument 40 may include electronic circuitry (not shown) such as that described in U.S. Pat. No. 5,182,513, entitled: "Method and Apparatus for Nondestructive Surface Flaw Detection" and U.S. Pat. No. 5,237,271 entitled: "Multi-Frequency Eddy Current Sensing" for receiving the signals from the sense coils 32 and for converting the signals to images for the detection of flaws or defects in the dovetail slot surface 12'. The eddy current instrument 40 may also include a signal generator (not shown) for energizing drive coils 30 or the signal generator may be a separate piece of equipment.

A layer 56 of moldable rubber, such as RTV as manufactured by Dow Corning may be disposed between the backing layer 24 and the expandable bar 20 to provide a layer 56 of compressible material to facilitate compliance or a close uniform fit between the eddy current array circuit 28 and the surface under inspection and to maintain the drive coils 30 and the sense coils 32 at a respective substantially constant distance from the component surface portion during scanning by the probe device 10 to thereby prevent the adverse effects of lift-off.

In accordance with the present invention, the expandable bar 20 has a slot 60 formed therein with the slot 60 having interior sides 62 which narrow toward the operating face 23 of the expandable bar 20. Referring to FIG. 2, the main slot 60 may be bifurcated on each end to form narrower longitudinal slots 60a, 60b, 60c and 60d. These bifurcated slots permit the opposite exterior side edges 21a and 21b of the expandable bar 20 to expand as will be described in more detail herein below to provide conformance between the eddy current array circuit 28 and the surface under inspection. It should also be noted that the interior side edges 62 of the main slot 60 narrow toward the operating face 23 at a predetermined slope.

An expanding wedge 66 is disposed partially within the slot 60 and is formed with angled side edges 68a and 68b which are angled at a selected slope to respectively matingly engage the interior sides 62 of the slot 60 to cause the exterior side edges 21a and 21b of the expandable bar 20 to expand outwardly when the wedge 66 is pushed deeper into the slot 60. The expandable bar 20 and the wedge 66 are preferably made from a hard insulative material, engineering plastic, such as Delrin ®, or the like to prevent interference with the eddy current signals.

The wedge 66 is connected to a pin 70 which extends up through a channel formed in the probe body extension member 18 and the probe body base 16. The pin 70 is coupled to an actuator 72 which applies a force to pin 70 to push the wedge 66 further into the slot 60 formed in the expandable bar 20 to cause the sides 21a and 21b of the expandable bar 20 to expand farther and to cause the array circuit 28 to conform to the surface under inspection as shown in FIG. 1B. The actuator may be any suitable device for extending and retracting pin 70 or may be the actuator described in detail in co-pending U.S. patent application Ser. No. 07/862,950, entitled: "An Eddy Current Device for Inspecting a Component".

In operation, the expandable bar 20 is extended from the probe extension member 18 by pins, similar to pin 70 and parallel therewith, and the actuator 72. The pins, similar to pin 70, are coupled to the expandable bar 20 by receipt holes or vias 74 shown in FIG. 2. Accordingly, after the array probe device 10 is positioned within a dovetail slot 12 for inspection, the actuator 72 may be activated to cause the expandable forming bar 20 to extend from the probe extension member 18 to cause lands 75 extending outwardly from the probe extension member 18 to engage the shoulders 76 of the dovetail slot 12 and to force the eddy current array circuit 28 into conformance with then again be activated to cause the pin 70 to force the base of the dovetail slot 12. The actuator 72 may the wedge 66 deeper into the slot 60 formed in the expandable bar 20 to cause the exterior side edges 21a and 21b against the interior walls of the dovetail slot 12 to provide compliance between the eddy current array circuit 28 and the side walls of the dovetail slot 12 for substantially complete inspection of the dovetail slot as the probe device 10 is moved or scanned along the slot 12.

Those skilled in the art will, therefore, recognize that the present invention provides a novel device for inspecting the dovetail slot of a gas turbine engine component or the like in a single scanning operation which prevents the problem of lift-off and provides a device which can be scanned across the slot and easily moved from one dovetail slot to another for efficient inspection of multiple slots normally found in components such as a disk of a gas turbine engine or the teeth of a gear.

While the present invention has been described primarily with application to inspecting dovetail slots of a gas turbine engine component, those skilled in the art will recognize that the principles of the present invention and the probe system described can easily be modified or adapted to inspect any component with a surface having a simple or complex geometric shape. Therefore, it will be readily understood by those skilled in the art that the present invention is not limited to the specific embodiments described and illustrated herein. Different embodiments and adaptations besides those shown herein and described as well as many variations, modifications and equivalent arrangements will now be apparent or will be reasonably suggested by the foregoing specification and drawings, without departing from the substance or scope of the invention. While the present invention has been described herein in detail in relation to its preferred embodiments, it is to be understood that this disclosure is only illustrative and exemplary of the present invention and is made merely for purposes of providing a full and enabling disclosure of the invention. Accordingly, it is intended that the invention be limited only by the spirit and scope of the claims appended hereto.

What is claimed is:

1. A device for inspecting a component, comprising:

an eddy current array circuit having respective pluralities of drive and sense elements and having an active face for positioning on a surface portion of the component during an inspection operation;

a backing disposed on a face of said eddy current array circuit opposite to said active face to apply a uniform pressure behind said array circuit to maintain the array circuit against the surface portion during the inspection operation;

an expandable bar having expandable exterior side edges and an operating face shaped to cause said eddy current array circuit to conform to the shape of the component surface under inspection, said eddy current array circuit and said backing being disposed over said operating face with said array circuit active face being closest to the component surface portion and said expandable bar having a slot formed therein, said slot having interior sides which narrow toward said operating face at a predetermined slope;

an expanding wedge with angled sides for respectively matingly engaging said interior sides of said slot to cause: said exterior side edges of said expandable bar to expand outwardly when said wedge is pushed deeper into said slot;

an actuator to push said wedge deeper into said slot; and means for electrically connecting said eddy current array circuit to an eddy current instrument.

2. The device of claim 1, further comprising a layer of compressible material disposed between said backing and said expandable bar to provide a close uniform fit between said eddy current array circuit and the surface of the component under inspection.

3. The device of claim 1, further comprising means for registering said eddy current array circuit relative to said expandable bar to provide accurate location and size information of any detected defect during an inspection operation.

4. The device of claim 1, wherein said backing has a plurality of longitudinal ridges formed therein in a face thereof adjacent to said expandable bar to facilitate disposition of said backing and said array circuit over said operating face and to prevent liftoff of said array circuit while sliding said array circuit along the component surface.

5. The device of claim 1, further comprising a sacrificial layer of material disposed over said array circuit active face to prevent wear of said active face and to facilitate sliding of said active face along the component surface portion during an inspection operation.

* * * * *